United States Patent [19]

McEntire

[11] Patent Number: 4,552,957
[45] Date of Patent: Nov. 12, 1985

[54] METHOD OF SEPARATING PRIMARY AMINES FROM TERTIARY AMINES USING NON-POLAR HYDROCARBON SOLVENT WITH OR WITHOUT POLYHYDROXYLIC COMPOUND

[75] Inventor: Edward E. McEntire, Austin, Tex.

[73] Assignee: Texaco Inc., White Plains, N.Y.

[21] Appl. No.: 581,465

[22] Filed: Feb. 17, 1984

[51] Int. Cl.$^4$ ............... C07D 265/30; C07D 265/32; C07D 295/12; C07C 87/00

[52] U.S. Cl. .................................. 544/177; 564/499; 564/437

[58] Field of Search ................ 544/177; 564/499, 437

[56] References Cited

U.S. PATENT DOCUMENTS

| | | | |
|---|---|---|---|
| 2,412,209 | 12/1946 | Dickey et al. | 564/493 X |
| 2,691,624 | 10/1954 | Challis | 564/499 |
| 3,033,864 | 5/1962 | Britton et al. | 544/358 |
| 3,038,904 | 6/1962 | Godfrey | 544/225 |
| 3,105,019 | 9/1963 | Murray et al. | 544/358 X |
| 3,151,113 | 9/1964 | Advani et al. | 544/106 |
| 3,417,141 | 12/1968 | Feldman et al. | 564/437 X |
| 3,420,828 | 1/1969 | Muhlbauer | 544/177 |

FOREIGN PATENT DOCUMENTS 1020513  2/1966  United Kingdom ............... 564/499

OTHER PUBLICATIONS

Ferguson—Textbook of Organic Chemistry, D. Van Nostrand Co., Aug. 1961.

Primary Examiner—John E. Kittle
Assistant Examiner—Mukund J. Shah
Attorney, Agent, or Firm—Jack H. Park; Kenneth R. Priem; Richard A. Morgan

[57]  ABSTRACT

A method for the separation of primary amines such as bis-(2-aminoethyl)ether from tertiary amines such as N-(2-methoxyethyl)morpholine which have close boiling points via extraction using a non-polar hydrocarbon solvent is described. Alternatively, a polyhydroxylic compound or a mixture of such compounds may be added to a stream containing both bis-(2-aminoethyl)ether and N-(2-methoxyethyl)morpholine before extraction with the non-polar hydrocarbon is performed. The N-(2-methoxyethyl)morpholine is selectively removed by the hydrocarbon.

14 Claims, No Drawings

METHOD OF SEPARATING PRIMARY AMINES FROM TERTIARY AMINES USING NON-POLAR HYDROCARBON SOLVENT WITH OR WITHOUT POLYHYDROXYLIC COMPOUND

BACKGROUND OF THE INVENTION

Cross-Reference to Related Application

This application is related to U.S. patent application Ser. No. 06/581,464, filed of even date which is concerned with a method for separating primary and tertiary amines with close boiling points using a non-polar hydrocarbon and water.

FIELD OF THE INVENTION

The invention relates to amine extractive separation methods and more particularly relates to methods for the separation of primary amines from tertiary amines which have close boiling points, by means of a non-polar hydrocarbon solvent.

DESCRIPTION OF OTHER RELEVANT METHODS IN THE FIELD

Bis-(2-amineothyl)ether (BAEE) and N-(2-methoxyethyl)morpholine (MEM) are co-products in the production of morpholine when diethylene glycol and ammonia are used as the reactor feed. These two co-products are very difficult to separate by conventional distillation because of their close boiling points. It would be advantageous to separate these two compounds because BAEE can be methylated to form $\beta$-(N,N-dimethylamino)alkyl ethers which are useful as catalysts in polyurethane isocyanate reactions according to U.S. Pat. No. 3,330,782, incorporated by reference herein.

No method has been found for the separation of these two compounds. However, amines have been separated from other compounds according to some of the following techniques.

For example, U.S. Pat. No. 3,033,864 discloses the purification of pyrazines and piperazines by azeotropic distillation. In that patent, the goal was to remove unreacted alkanolamines by using codistillation agents comprising aliphatic hydrocarbons, aromatic hydrocarbons and nuclear chlorinated aromatic hydrocarbons having normal boiling points between about 130° and 200° C. Representative examples given were octane and higher aliphatic hydrocarbons, petroleum fraction mixtures, ethyl cyclohexane, ethylbenzene, the xylenes, diethylbenzene, ethyl toluene, cumene and chlorobenzene.

A process for recovering piperazine from a mixture with triethylenediamine is described in U.S. Pat. No. 3,105,019. The inventors therein found that aliphatic hydrocarbons and especially saturated aliphatic hydrocarbons would be suitable azeotropic agents for the piperazine-triethylenediamine split if the boiling points were in the range from 110° C. to about 200° C., with particularly good results being obtained if the boiling point is within the range from about 140° C. to about 160° C. Specific compounds mentioned and tried were 3-methylheptane, 2-ethyl hexane, 1,2-dimethyl cyclohexane, meta-xylene, nonane, styrene, mesitylene, kerosene and 1-methyl naphthalene.

A method if recovering the major by-products from piperazine reaction residue is presented in U.S. Pat. No. 3,331,756. It was taught therein that hydrocarbons immiscible with diethylenetriamine and boiling within the range of about 175° to about 250° C. would be suitable entrainers for use in the separation of diethylenetriamine and aminoethylpiperazine. Two azeotropic agents mentioned were tetrapropylene and n-dodecane, with tetrapropylene being preferred because it gave a cleaner separation.

Russian Pat. No. 472,122 teaches that diethylenetriamine and aminoethylpiperazine may be separated from reaction mixtures (especially those from the synthesis of a diamine and piperazine) by means of azeotropic rectification using a hydrocarbon mixture boiling at 160° to 174° C. yielding an azeotrope with DETA. The inventors found that the fractionation is simpler with n-decane than with dodecane or tetrapropylene.

The separation of an alkylene open chain polyamine from a piperazine compound may be accomplished by complexing the polyamine with a salt selected from the group consisting of sulfates and chlorides of copper, nickel, cobalt and zinc, according to the invention disclosed in U.S. Pat. No. 3,038,904. The complex compounds are extracted with substances such as chloroform or are allowed to precipitate out. U.S. Pat. No. 3,400,129 reveals that 2- methyl triethylenediamine can be purified in a process which incorporates a two-solvent extraction step. One of the solvents is water and the other is an organic solvent for pyrazines, such as hexene, octene, nonene, benzene, toluene, xylenes, ethyl benzene, propyl benzene, n-hexane, n-heptane, isooctane, n-nonane, methylnonane, chlorobenzene, chlorotoluenes, diethylether, furan and alkylbenzonitriles. The method includes an azeotropic distillation step where 2-methylpiperazine is distilled and a step where the purified 2-methyl triethylenediamine is recovered.

Further, in Advances in Chemistry Series No. 116: Azeotropic Data III, 1973, L. H. Horsley lists a number of binary azeotropic systems.

SUMMARY OF THE INVENTION

The invention relates to a method for the separation of a primary amine from a tertiary amine, both amines having close boiling points, by extracting a mixture containing both compounds with a non-polar hydrocarbon to selectively remove the tertiary amine with the hydrocarbon.

DETAILED DESCRIPTION OF THE PREFERRED EMBODIMENTS

The method of this invention will be effective for any separation of a tertiary amine from a primary amine where the amines have close boiling points. For purposes of this discussion, the amines have close boiling points if the materials boil within about 5° C. of each other. Of course, if the boiling points are not very close, the amines may be separated by the simpler process of conventional distillation.

The addition of a non-polar hydrocarbon solvent helps to entrain the tertiary amine. The tertiary amine has all of the nitrogen valences occupied and is, therefore, relatively non-polar as compared with the primary amine which has only one substituent on the nitrogen atom. Two amines which fulfill the requirements set out above are bis-(2-aminoethyl)ether and N-(2-methoxyethyl)morpholine.

Bis-(2-aminoethyl)ether (BAEE) and N-(2-methoxyethyl)morpholine (MEM) are both by-products in the production of morpholine from diethylene glycol and ammonia. This method of producing morpholine is referred to in U.S. Pat. Nos. 2,412,209 and 3,151,112, incorporated by reference herein. However, BAEE and MEM are difficult to separate from each other by conventional distillation.

The method of this invention allows for separating these two co-products so that both may be productively used. The method has two alternate approaches, the first of which involves extraction of the mixed co-product stream with a nonpolar hydrocarbon, such as cyclohexane, which selectively removes MEM from the mixture. The second technique involves the addition of a polyhydroxylic compound (or a mixture of polyhydroxylic compounds) to the co-product stream, then extracting with a relatively non-polar solvent. The MEM is extracted into the relatively non-polar phase, leaving the BAEE in the polar phase. Once the BAEE and the MEM have been isolated into separate phases, each can be recovered individually by conventional distillation.

In the first alternate method, the non-polar hydrocarbons may be linear or branched, cyclic or containing cyclic moieties. The solvent may be any aliphatic, aromatic or alkaryl hydrocarbon having from 1 to 30 carbon atoms and also similarly sized halocarbons which are unreactive with the amines of the mixture to be separated. Examples of suitable solvents are methane, butane, isopentane, cyclohexane, heptane, dodecane, dodecene, kerosene, mineral oil, etc. The polarity of the solvent used should be less than that of toluene.

The second alternative method may use all of the non-polar hydrocarbons of the first alternative as well as other suitable solvents such as toluene, chlorobenzene, unreactive aromatic solvents and mixtures of any of the above. The polyhydroxylic materials of the second alternative may be any compound or mixture of compounds having two or more hydroxyl functions such as ethylene glycol, propylene glycol, diethylene glycol, glycerine, sorbitol, etc. which are soluble in the co-product stream. The total carbon atom content in these materials should not exceed two carbon atoms for each oxygen function. These polyhydroxylic materials may contain up to about 50% water or methanol and still be effective. The non-polar and polyhydroxylic solvent of both alternatives should be employed in excess quantities, although economic considerations for this novel extraction process will set an upper limit on the amount of solvents which can be used.

The process may be conducted at or near ambient temperatures. The method would be useful throughout temperature and pressure conditions from the freezing point of the amine mixture to the approximate boiling point of the mixture. These extractive solvents may even be useful above the critical point of the mixture. Selectivity to the separation concentration would be dependent on temperature, but would not vary with the pressure.

The invention will be further illustrated by the following examples.

EXAMPLE 1

This example illustrates the first alternative of the inventive method.

A sample of morpholine co-product stream was heated in a flask with an efficient distillation column to a pot temperature of 190° C. to remove water. This stripped liquid contained 24% MEM and 67% BAEE, with 2.2% morpholine, 1.5% monoethanolamine, 0.4% ethylene glycol, 3.9% aminoethylmorpholine, 0.4% 2-(2-aminoethoxy)ethanol, with the remainder comprising unknown materials.

Extraction of 254 g of the mixture with 465 g of cyclohexane three times left 90 g of a polar phase containing 81.6% BAEE, 1.24% MEM, 4% monoethanolamine, 0.7% morpholine, 1.6% ethylene glycol, 1.2% aminoethylmorpholine and 2.1% 2-(2-aminoethoxy)ethanol, with the remainder being composed of cyclohexane and unknowns. The MEM was extracted into the cyclohexane more selectively than was BAEE.

Analysis was performed by gas-liquid chromatography on a Carbowax 20M on Chromosorb WHP column in this and subsequent examples.

EXAMPLE 2

The second alternate method, employing polar polyhydroxylic compounds, is illustrated in this example.

To 10 g of the crude co-product stream containing 23% MEM, 61% BAEE, 1% water, 5% morpholine, 2% monoethanolamine, 0.8% ethylene glycol, 5% aminoethylmorpholine and 1.5% aminoethoxyethanol (remainder unknowns) were added 20 g of toluene and 20 g of glycerine. After equilibrating by shaking, the rapidly separating phases were analyzed by gas-liquid chromatography. The results of this extraction and two other similar extractions are shown below.

| Extractant Pair, (g) | Area % MEM in Non-polar Phase | Ratio MEM to BAEE Non-polar Phase | A % BAEE in Polar Phase | Ratio BAEE to MEM in Polar Phase |
|---|---|---|---|---|
| a. Toluene (20) Glycerine (20) | 11.7 | 100 | — | — |
| b. Heptane (20) Methanol (20) | 2.5 | 100 | 18.2 | 3 |
| c. Chlorobenzene (20) Ethylene Glycol (15) | 9.3 | 34 | 22.0 | 10 |

All of the solvent pairs caused rapid separation of phases following mixing with the co-product stream.

EXAMPLE 3

In a separatory funnel were combined 173 g of the stripped co-product stream of Example 1, 280 g of water and 500 ml of toluene. The contents were shaken to equilibrate following a slow phase separation, and each phase analyzed as above by gas-liquid chromatography.

| Non-polar Phase | | Polar Phase | |
|---|---|---|---|
| Area % MEM | MEM:BAEE | Area % BAEE | BAEE:MEM |
| 4.6 | 66 | 18.2 | 4.6 |

EXAMPLE 4

To a separatory funnel were added 200 g of stripped co-product stream used in Example 1 and 400 g of glycerine. The resulting solution was extracted three times with 400 ml of toluene. The final non-polar phase weighed 542 g and contained 26% BAEE by gas-liquid chromatography, and only 1.5% MEM. The ratio of MEM:BAEE in the three separated non-polar phases was always greater than 100.

EXAMPLE 5

Two grams of the stripped co-product stream of Example 1 were combined with 5 g of toluene and 5 g of diethylene glycol. After equilibration by shaking, the polar phase contained 15.1% BAEE (BAEE:MEM=3.9) and the non-polar phase contained 7.7% MEM (MEM:BAEE=96).

The above examples illustrate that MEM and BAEE may be separated by either extraction technique. Although only batch equipment was used in these extractions, continuous or continuous countercurrent apparatus may be used also.

Many modifications may be made in the method of this invention by one skilled in the art without departing from the spirit and scope of the inventive method which is defined only by the appended claims. For example, one might adjust the temperature or find a precise combination of solvents which gives a particularly advantageous result.

I claim:

1. A method for the separation of primary and tertiary amines having close boiling points comprising
   extracting a mixture comprising a primary amine and a tertiary amine having close boiling points with a non-polar hydrocarbon selected from the group consisting of aliphatic, aromatic and alkylaryl hydrocarbons and unreactive halocarbons which have from 1 to 30 carbon atoms to selectively remove the tertiary amine with the non-polar hydrocarbon.

2. The method of claim 1 in which the non-polar hydrocarbon is selected from the group consisting of methane, butane, isopentane, cyclohexane, heptane, dodecane, dodecene, kerosene and mineral oil.

3. The method of claim 1 in which a polyhydroxylic compound is added to the amine mixture before the extraction.

4. The method of claim 3 in which the polyhydroxylic compound has at least two hydroxyl functions and has no more than two carbon atoms for each oxygen function.

5. The method of claim 3 in which the polyhydroxylic compound is selected from the group consisting of ethylene glycol, propylene glycol, diethylene glycol, glycerine and sorbitol.

6. The method of claim 1 in which the extraction is carried out at a temperature between about the freezing point and about the boiling point of the amine mixture.

7. A method for the separation of bis-(2-aminoethyl)ether from N-(2-methoxyethyl)morpholine consisting essentially of
   extracting a mixture comprising bis-(2-aminoethyl)ether and N-(2-methoxyethyl)morpholine with a non-polar hydrocarbon selected from the group consisting of aliphatic, aromatic and alkylaryl hydrocarbons and unreactive halocarbons which have from 1 to 30 carbon atoms to selectively remove the N-(2-methoxyethyl)morpholine with the non-polar hydrocarbon.

8. The method of claim 7 in which the non-polar hydrocarbon is selected from the group consisting of methane, butane, isopentane, cyclohexane, heptane, dodecane, dodecene, kerosene and mineral oil.

9. The method of claim 7 in which the method is carried out at a temperature between about the freezing point and about the boiling point of the amine mixture.

10. A method for the separation of bis-(2-aminoethyl)ether from N-(2-methoxyethyl)morpholine comprising
    a. adding to a mixture containing primarily bis-(2-aminoethyl)ether and N-(2-methoxyethyl)morpholine a polyhydroxylic compound or a mixture of polyhydroxylic compounds and
    b. extracting the mixture with a non-polar hydrocarbon selected from the group consisting of aliphatic, aromatic and alkylaryl hydrocarbons and unreactive halocarbons which have from 1 to 30 carbon atoms to selectively remove the N-(2-methoxyethyl)morpholine.

11. The method of claim 10 in which the polyhydroxylic compound has at least two hydroxyl functions and has no more than two carbon atoms for each oxygen function.

12. The method of claim 10 in which the polyhydroxylic compound is selected from the group consisting of ethylene glycol, propylene glycol, diethylene glycol, glycerine and sorbitol.

13. The method of claim 10 in which the non-polar hydrocarbon is selected from the group consisting of methane, butane, isopentane, cyclohexane, heptane, dodecane, dodecene, kerosene, mineral oil, toluene and chlorobenzene.

14. The method of claim 10 in which the extraction step is carried out at a temperature between about the freezing point and about the boiling point of the amine mixture.

* * * * *